United States Patent [19]

Heckenberg et al.

[11] Patent Number: 5,279,972
[45] Date of Patent: Jan. 18, 1994

[54] PROCESS FOR ANALYZING SAMPLES FOR ION ANALYSIS

[75] Inventors: Allan L. Heckenberg, Providence, R.I.; Peter P. Jandik, Framingham, Mass.; William Jones, Blackstone, Mass.; Robert Lawrence, III, Milford, Mass.

[73] Assignee: Millipore Corporation, Bedford, Mass.

[21] Appl. No.: 827,190

[22] Filed: Jan. 28, 1992

Related U.S. Application Data

[60] Division of Ser. No. 318,034, Mar. 2, 1989, abandoned, which is a continuation-in-part of Ser. No. 249,011, Sep. 26, 1988, abandoned.

[51] Int. Cl.⁵ .................. G01N 30/02; G01N 30/14; B01D 63/04
[52] U.S. Cl. .................. 436/178; 210/500.23; 210/500.37; 210/638; 210/641; 210/650; 210/653; 210/656; 422/70; 436/161; 436/177
[58] Field of Search .................. 210/500.23, 500.27, 210/500.37, 638, 641, 650, 653, 656, 678, 686; 436/79, 177, 178, 161; 422/70

[56] References Cited

U.S. PATENT DOCUMENTS

| | | | |
|---|---|---|---|
| 4,451,374 | 5/1984 | Peterson et al. | 422/70 X |
| 4,474,664 | 10/1984 | Stevens et al. | 210/656 |
| 4,549,965 | 10/1985 | Davis | 422/70 X |
| 4,584,276 | 4/1988 | Hanaoka et al. | 436/161 X |
| 4,647,380 | 3/1987 | Dasgupta | 210/638 |
| 4,727,034 | 2/1988 | Matsushita et al. | 436/161 |
| 4,775,476 | 10/1988 | Melcher et al. | 436/161 X |
| 4,837,157 | 6/1989 | Turnell et al. | 436/161 X |
| 4,913,817 | 4/1990 | Tsushima et al. | 201/500.27 |

OTHER PUBLICATIONS

Jones et al., "Elimination of Matrix Interferences in Ion Chromatographic Analysis of Difficult Aqueous Samples", J. of Chromatographic Sc., 27, 1989, 449–455.

Primary Examiner—James C. Housel
Assistant Examiner—Milton I. Cano
Attorney, Agent, or Firm—Andrew T. Karnakis; Paul J. Cook

[57] ABSTRACT

A sample preparation process and apparatus are provided for samples to be analyzed subsequently, such as by liquid chromatography. The sample is passed in contact with an ion exchange polymer which is characterized by being capable of facilitating removal of one or more undesired ions from the sample to be replaced with an ion transferred from the bound exchange site of the polymer and through the polymer. The polymer is prewashed with water to remove substantially all leachable species from the polymer. In one embodiment, the polymer is coated with a color indicator capable of changing color when the polymer is depleted of the ion to be transferred therefrom. The ion exchange capacity of the apparatus can be significantly expanded by using a counter ion donating solution capable of replacing the bound ions at the ion exchange sites as they become exchanged for the undesired ions from the sample.

16 Claims, 9 Drawing Sheets

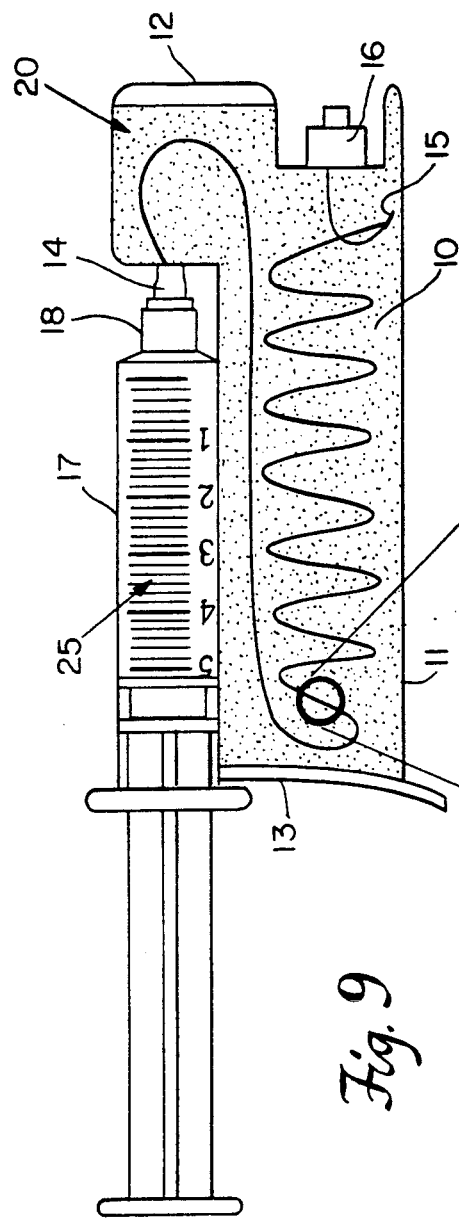
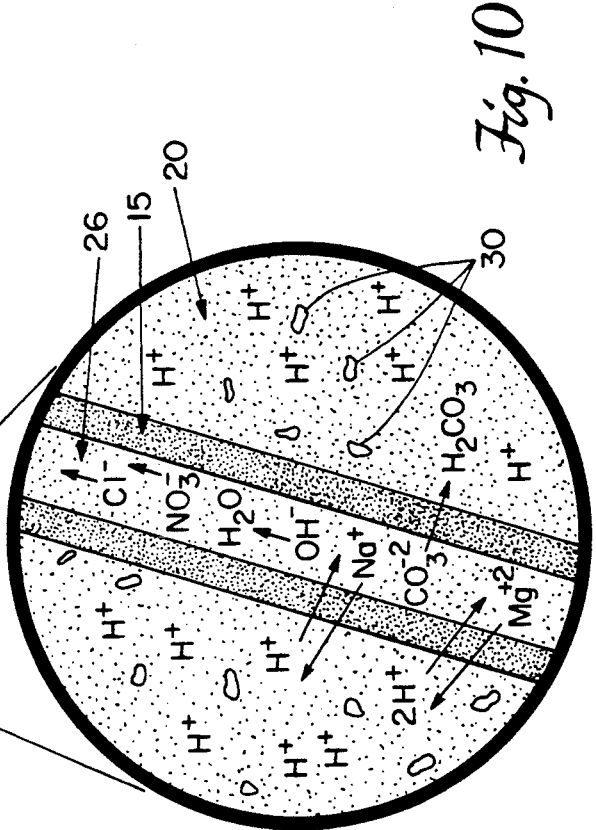
Fig. 9
Fig. 10

PROCESS FOR ANALYZING SAMPLES FOR ION ANALYSIS

REFERENCE TO RELATED APPLICATION

This is a divisional of copending application Ser. No. 318,034 filed on Mar. 2, 1989, now abandoned, which is a continuation-in-part application of application Ser. No. 249,011, filed Sep. 26, 1988, now abandoned.

BACKGROUND OF THE INVENTION

This invention relates to a process and apparatus for preparing samples to be analyzed for ionic species such as by liquid column chromatography.

At the present time, it is known that several typical liquid samples containing ionic species cause serious problems when analyzed by ion chromatography apparatus. Included in these samples are those having a pH value greater than pH 10 or lower than pH 4, samples with high carbonate concentration and samples containing high concentrations of divalent cations such as calcium and/or magnesium. Presently these samples are prepared for subsequent analysis by adding thereto acidic or basic solutions in order to permit identification of the ionic species for which the analysis is being made without interference by other ionic species in solution. These sample preparation processes are undesirable since they introduce significant interference from the counter ions from the added acid (anions) or base (cations). This can cause considerable interference which can limit the capability of the analysis apparatus to properly determine the individual constituents and their amounts in the sample.

Attempts to utilize ion exchange resin beads to remove undesired ions is an improvement in that it eliminates the addition of excessive counter ions as these counter ions are covalently bound to the bead. In this process, the sample volume selected for analysis is passed through, on or over the polymeric like structure which includes counter ions bonded to either a silicate or an organic polymer bead. The potentially interfering counter ions are sufficiently bonded to the beads as to preclude direct analytical interference. However, the beads are themselves a source of organic and inorganic contamination. Even a repeated and very extensive precleaning of the ion exchange resin beads does not prevent sample contamination at the levels detachable by presently available ion chromatography apparatus. In addition, the resin beads have adsorption-desorption capacity so that a portion of the ions being analyzed are adsorbed into the pores of the resin beads. The net effect is the possibility of skewing and/or loss of the resultant data during the analytical process thereby negating any anticipated advantage by selecting these materials as a means for improving the chromatographic analytical process.

It has also been known prior to this invention to utilize hollow fibers having an ion exchange capacity to purify a continuous stream of a gas passing therethrough.

A hollow fiber is defined as a seamless thin walled member of essentially tubular geometry with an inlet and outlet means where the constituent to be purified or reacted upon is communicated into the center of the tubular membrane system through the inlet, subsequently acted upon in a chemical manner by the tubular portion itself and/or by other reacting mechanism(s) present during the time the constituent is residing in the tubular portion of the fiber and subsequently removed through or passed from the tubular geometry by or through the outlet means. Such hollow fiber systems may be of singular or multiple path geometries and may also be immersed in solutions and/or gasses or connected with systems designed to promote the exchange process. An example is the use of sulfuric acid surrounding a hollow fiber to promote the exchange of protons across the hollow fiber tubular member portion. Such an added solution to a hollow fiber system component in this way is defined as a counter ion donating solution or CIDS. However, it is also known that the solution comprising the source of regenerated ions can penetrate the hollow fibers such that the proton donator, e.g., sulfuric acid, contaminates the liquid by passing sulfate ions through the hollow fiber.

Accordingly, it would be desirable to provide a method for effecting sample preparation for ion analysis without the need for adding an acidic or basic solution to the sample since such prior art methods introduce significant interferences into the sample. In addition, it would be desirable to provide such a method wherein impurities from the ion exchange medium into the sample are eliminated. Furthermore, it would be desirable to provide such a sample preparation means which can be used with a wide variety of liquid samples. In addition, it would be desirable to provide a sample preparation means which can rapidly process a large number of samples before being replaced. Also, it would be desirable to provide a sample preparation means which provides a simple means by which the operator can replace depleted ion exchange polymer.

SUMMARY OF THE INVENTION

The present invention is based upon the discovery that ion exchange hollow fibers or membranes capable of passing ions therethrough while preventing larger undesirable molecules and certain charted ions from passing therethrough can be treated to be rendered capable of removing unwanted ions from a liquid sample or of a pH adjustment of a liquid sample without introducing impurities into the liquid sample which adversely affect subsequent ion analysis of the liquid sample. The polymer is functionalized with the appropriate ion or ions and can be immersed in an environment such as a solution which provides a source of additional appropriate ion or ions. The liquid sample, thus treated, can be introduced into any conventional ion analysis system for analysis without introducing impurities into the analysis system or adversely reducing the usefulness of the ion analysis system by virtue of the presence of excess undesired ions. In accordance with this invention, the ion exchange fibers or membranes utilized in the present invention are washed for a period of time lasting only about several seconds up to a minute such as in deionized water or in a preliminary volume portion of the sample in a one step or two step washing procedure. Thereafter, the ion-exchange fiber or membrane is utilized to pre-treat a sample in accordance with this invention. The ion exchange fibers or membranes which have been treated by washing can be immersed in an ion donating solution without migration of that part of the donor molecule that caries the same type of charge as the ionic groups of the polymer molecule into the liquid sample being processed with the fiber or membrane. The ion exchange membrane also can be modified to include a color indicator which effects a color change when the fiber or membrane is depleted of donating cation or anion.

The present invention also provides an apparatus comprising a housing structure for one or more hollow fibers or membranes, inlet and outlet fitments to provide easy communication of the sample to the fiber or a space between adjacent membranes. Optionally, the hollow fiber, flat membrane or CIDS can include an indicator component which provides visual reference as to the viability of the fiber or membrane or the ion donating solution to contribute additional ions to the active fiber or membrane.

BRIEF DESCRIPTION OF THE DRAWINGS

FIG. 9 is a cross-sectional representation of a preferred embodiment of a device utilizing a hollow ion exchange fiber component immersed in a counter-ion donating environment.

FIG. 10 is a close-up detail showing a typical ionic exchange medium utilizing a hollow ion exchange fiber component immersed in a counter-ion donating environment.

DETAILED DESCRIPTION OF SPECIFIC EMBODIMENTS

Figure 1A:
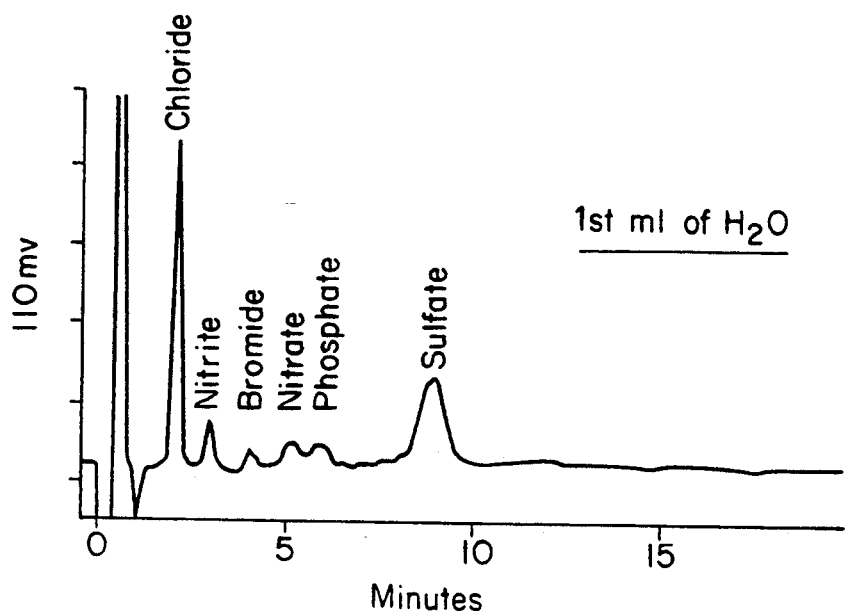
FIGS. 1a-1c are ion chromatograms of a deionized water sample passed through a sulfonated perfluorinated polymeric ion exchange hollow fiber immersed in deionized water.

As used herein the term "sample" means a small randomly selected homogeneous portion of a larger entity utilized to evaluate and/or to ascertain the constituent components of the larger entity. It is a direct correlatable representation of the overall composition of the larger entity.

In accordance with the present invention, ion exchange hollow fibers or membranes are treated by washing such as in deionized water in order to render them useful for the pretreatment of samples to be analyzed subsequently by ion analysis such as liquid chromatography, inductively coupled plasma atomic emission spectroscopy, nuclear magnetic resonance or the like. The ion exchange resins which are not useful in the present invention can not be rendered free of impurities by washing in deionized water even when the washing is effected for hours. Ion exclusion processes cause loss of certain ions due to adsorption. In contrast, the ion exchange fibers or membranes useful in the present invention can be rendered free of impurities that are leached into a liquid sample by washing with deionized water or with a volume of the sample in a matter of only several seconds either in a one or two step process along with the minimization of exclusion effects. That is, the fibers are substantially free of water leachable species to the extent that there is no interference to a subsequently employed analytical process.

Previously membranes were used to prevent migration of large molecules from one compartment to another. In these prior applications (reverse osmosis, hemodialysis) molecular size is the only important parameter. In this invention, suitable membranes are capable of excluding ions carrying certain charge from penetration wile at the same time ions carrying the opposite charge to those ions being excluded are allowed to permeate freely through the membrane material.

Representative suitable ion exchange fibers or membranes in the present invention include perfluorinated ion exchange polymers such as those in the sulfonated or aminated form sold under the tradename, Nafion by E. I. duPont de Nemours and Company, ion exchange functionalized cellulose acetate, ion exchange functionalized polytetrafluoroethylenes and the like ion exchange functionalized polymers. The ion exchange fibers or membranes useful in the present invention are capable of exchanging cations such as sodium, calcium or magnesium in the sample or the like with hydrogen ions of the membrane or of exchanging ions as hydroxide for anions in the sample such as chloride, nitrate or sulfate. Furthermore, the ion exchange fibers or membranes of the present invention are capable of exchanging an alkali metal ion, for excess hydrogen ion in the sample in order to increase pH of the sample prior to introduction of the sample into an ion analysis process.

In the present invention, the ion exchange fibers or membranes are washed in a solution such as deionized water or an initial portion of a sample. Washing beyond about 1 minute is unnecessary in order to reduce the impurities in the ion exchange fibers or membranes to a suitable level in accordance with this invention.

By reducing the undesired ion concentration of the sample which may be analyzed by ion analysis, the ion analysis apparatus is not undesirably affected by anomalies of excess concentrations of these ions. In one aspect of this invention, the hollow fiber or flat sheet membrane can be immersed in an ion donating solution in order to maintain the desired levels of donor ion into the sample such as hydrogen ion or sodium ion. Suitable ion donating solutions for providing hydrogen ions include acids such as octane sulfonic acid. Suitable ion donating solutions for providing an alkali metal ion in order to increase the pH of the sample include alkali metal sulfonates. Thus the pH of the sample can be raised or lowered.

Representative ionic function for cation exchange polymer include sulfonate, carboxylate and immobilized iminodiacetic acid (IDA) or ethylenediaminetetraacetic acid (EDTA) such as in the proton form or in the alkali metal form. The latter can be utilized to chelate metals from the sample such as transition metals. Representative cations which can be removed from the sample include group IA and II A cations, transition metals, lanthanides; actinides; mono-, di-, tri- and quaternary amines, ethanolamines and some positively charged cation complexes. The polymer also can be converted to a form other than a proton form or alkali metal form. Thus the silver form can be utilized to precipitate chloride or other halogens as Ag-halides. The barium form can be utilized to precipitate chromate. The bismuth form can be utilized to precipitate phosphate. The iron form can be utilized to complex with phosphates or with some chelating species, e.g., tartaric, citric acid or EDTA.

Representative ionic functions for anion exchange polymers include amine, dialkylamine, quaternary amine or the like. These fibers are capable of exchanging a bound hydroxyl group for an anion in solution which can contain acids or bases, organic solvents, dissolved polymers or complexed metallics. These fibers also can be immersed in a counter ion donating solution for donating anions, e.g., hydroxyl. Also, a plurality of fibers can be utilized in series, e.g., one donating an hydroxy ion, e.g., to raise pH and e.g., a second donating a nitrate ion, e.g., to lower pH. In order to determine whether a CID solution has been depleted, a standard indication, such as a color indicator can be utilized to signal when replenishment or disposal should be effected.

The process of this invention also can be utilized to precondition non aqueous samples, such as alcohols, ketones, aldehydes, acetonitrile or the like. In addition, the process of this invention can be utilized to concentrate samples by retention of a particular ionic species on the polymer surface followed by elution with an acid or base when the polymer is not immersed in an ion donation solution (dry).

In one aspect of this invention, the ion exchange membrane or hollow fiber is coated with a color indicator composite which changes color when the ion donated by the membrane or fiber is depleted and is not available for introduction into the sample. Only color indicators capable of being adsorbed by the membrane material and which change color upon ion depletion can be utilized. A representative example of a color indicator includes Orange IV(4-anilinophenylazobenzenesulfonic acid) or tropaeolin 00 which changes color from dark red or violet at pH 1.3 or lower to a clear yellow at a weakly acidic or alkaline pH. At interim pH the color comprises various shades of orange red to orange yellow. Thus, this indicator can be used to show depletion of hydrogen ions. Since depletion of the donating ion will occur upstream within the treating apparatus, that portion of the membrane or fiber which first contacts the sample will change color first. The membrane or fiber including the donating ion is coated with a color indicator by immersing it in a solution of the color indicator until the membrane or fiber changes a color associated with the pH value for the fiber. The membrane or fiber is removed from solution and dried. Other representative suitable color indicators include methyl oranges and thymol blue which change color from red to yellow to the degree that its sulfonic groups are converted from the hydrogen to another form.

Figure 1B:
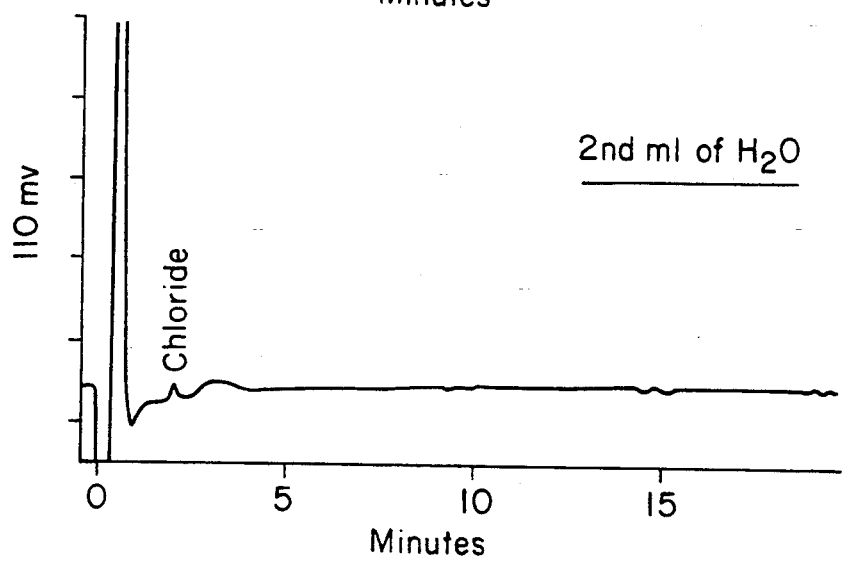
Figure 1C:
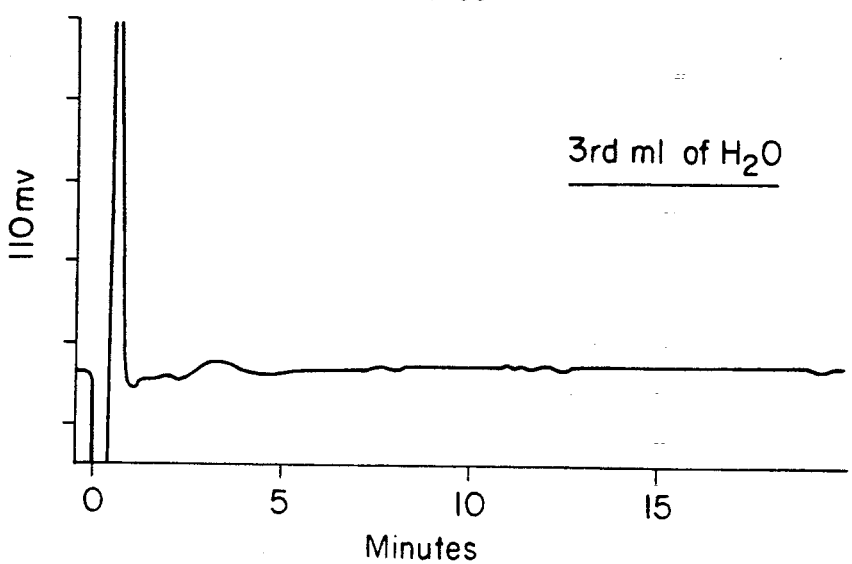

Referring to FIGS. 1a, 1b and 1c, the chromatographic results are shown. FIG. 1a shows the ion concentration in the first milliliter of deionized water. FIG. 1b shows the ion concentrations in the second milliliter of deionized water. FIG. 1c shows the ion concentrations in the third milliliter of deionized water. Injection volume for all three chromatographs was 100 ul. As shown in FIGS. 1a–1c, only two milliliters of deionized water are required to remove leachable impurities from the sulfonated form of perfluorinated ion exchange Nafion ion exchange fiber.

Figure 2A:
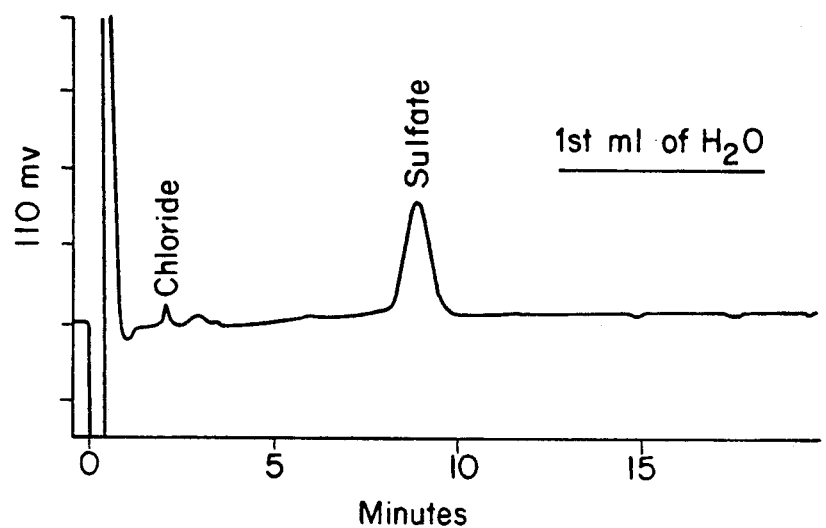
FIGS. 2a-2c are ion chromatograms of a deionized water sample passed through a sulfonated perfluorinated polymeric ion exchange hollow fiber immersed in 0.025N sulfuric acid.
Figure 2B:
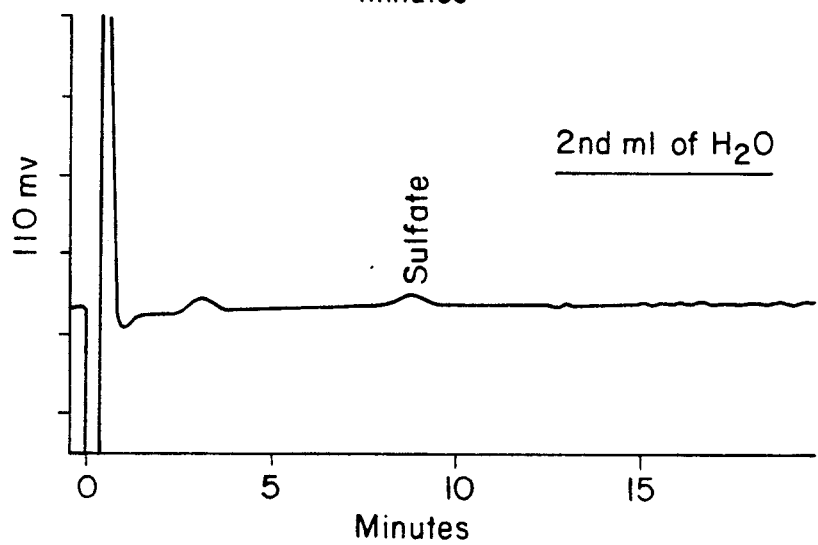
Figure 2C:
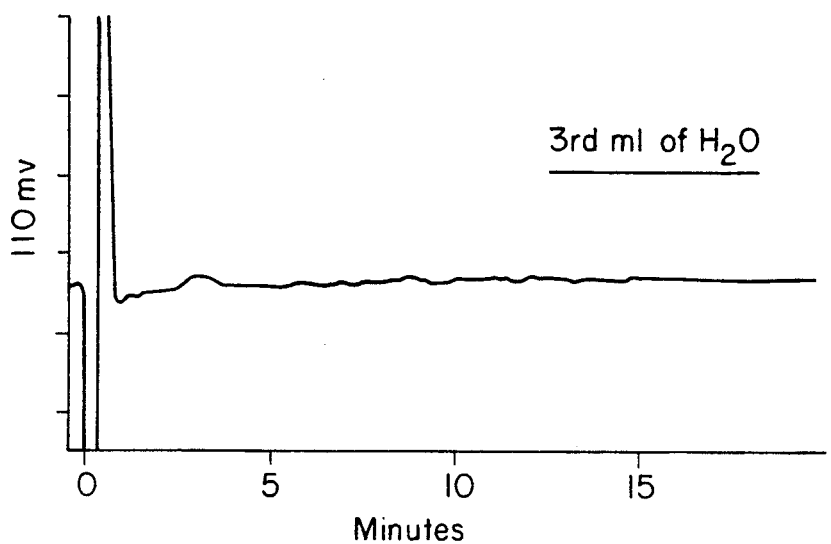

Referring to FIGS. 2a, 2b and 2c, the results of rinsing of the ion exchange hollow Nafion fiber described above which is immersed in a 0.025N sulfuric acid proton donor solution are shown. Deionized water is introduced in three 1 ml steps. From each one of these three steps 100 ul fractions are injected into ion chromatography. As shown in FIGS. 2a, 2b and 2c, the fiber is free of leachable ion after having passed therethrough only 2 ml of deionized water.

Figure 3A:
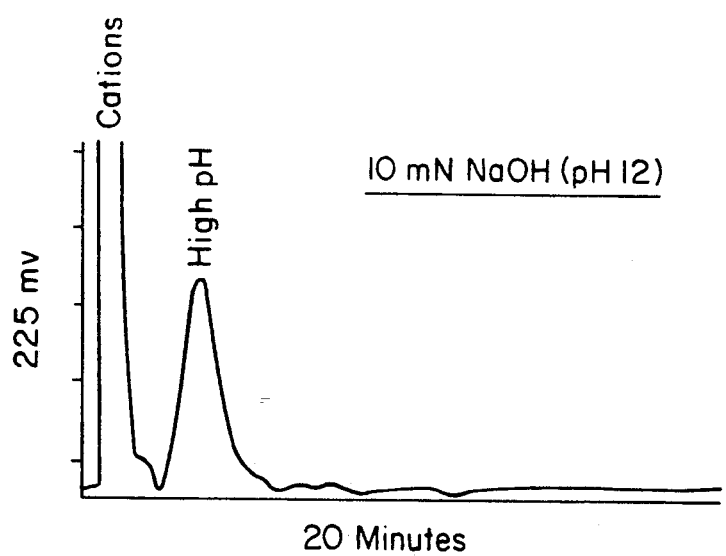
FIGS. 3a-3c are ion chromatograms of a pure matrix solution (10 nM NaOH) (3a) and of a standard dissolved in 10 ml NaOH obtained before (3b) and after (3c) they were passed through a sulfonated perfluorinated polymeric ion exchange hollow fiber immersed.
Figure 3B:
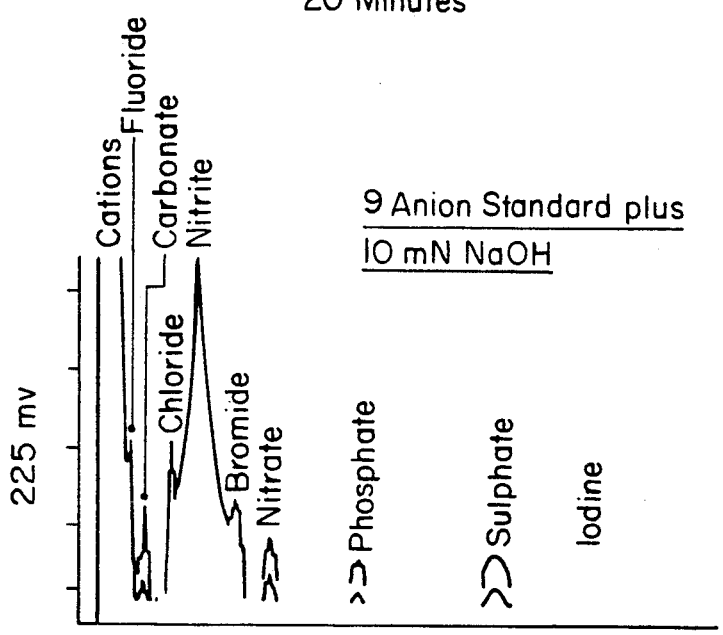
Figure 3C:
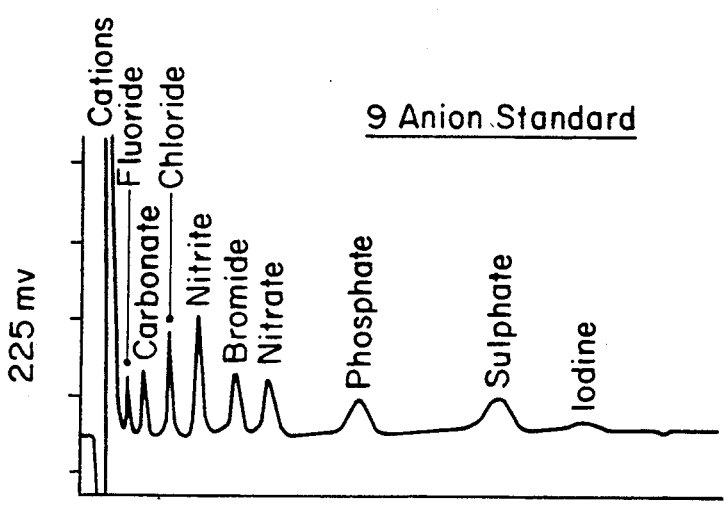

FIGS. 3a and 3b show typical distortions caused by excess sodium and hydroxyl ions. FIG. 3b is a chromatogram of a 9 anion standard sample plus excess sodium and hydroxyl ions. FIG. 3c shows a typical undistorted chromatogram of the 9 anion standard obtained after passing the sample from FIG. 3b through a H+ form cation exchange fiber immersed in a CID solution. As shown in FIGS. 3a–3c, it is necessary to remove excess sodium and hydroxyl ion in order to minimize or prevent distortion of an ion chromatographic recording.

Figure 4A:
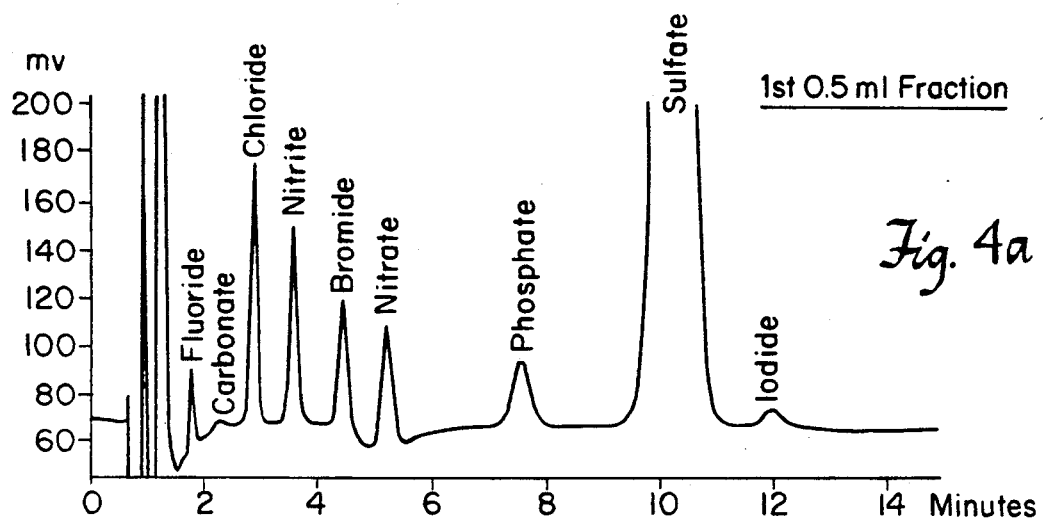
FIGS. 4a-4c are ion chromatograms of an aqueous standard solution passed through a sulfonated perfluorinated polymeric ion exchange hollow fiber immersed in 0.025N sulfuric acid.
Figure 4B:
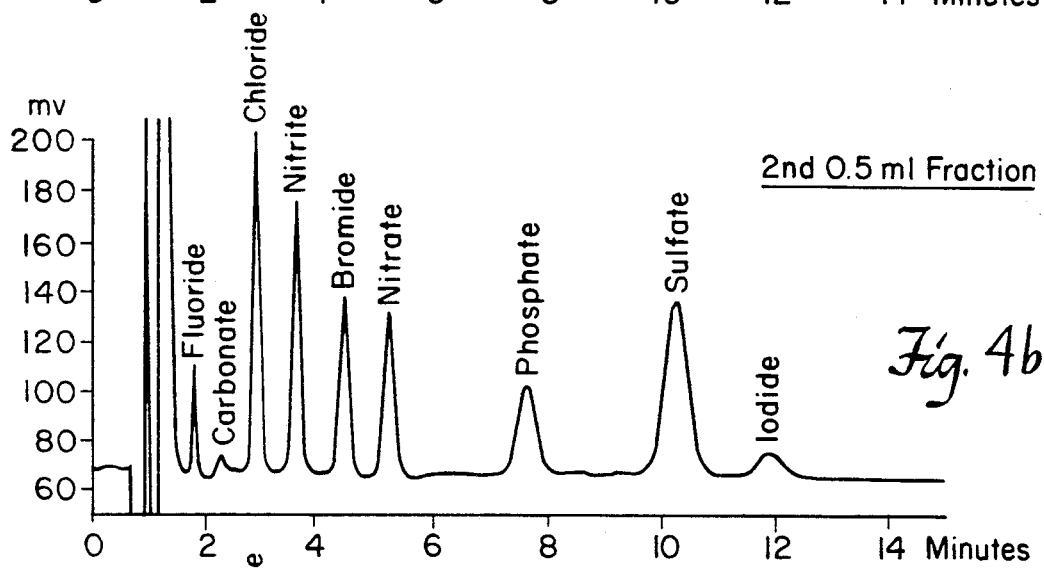
Figure 4C:
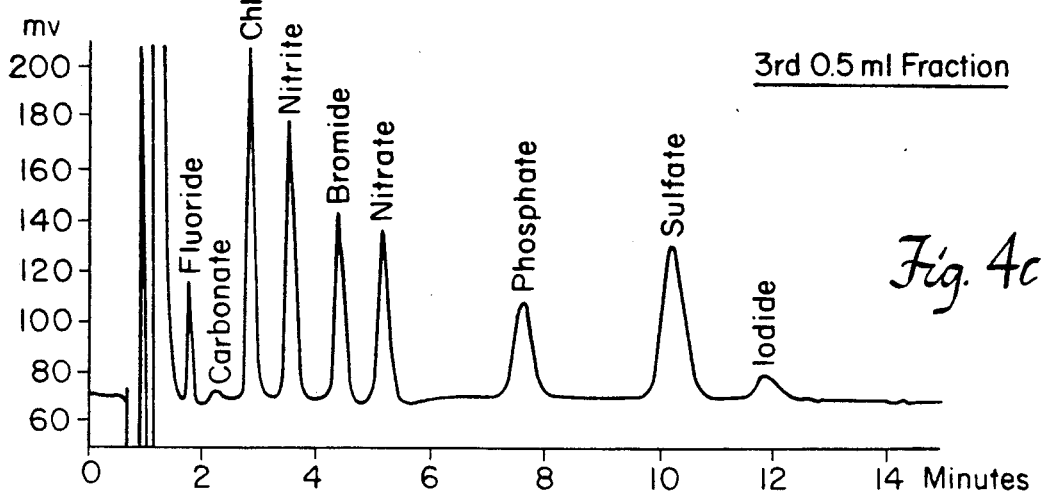

Referring to FIGS. 4a, 4b and 4c, ion chromatograms are shown for samples which are passed through a sulfonated perfluorinated (i.e., Nafion) ion exchange fiber which was washed by the procedure set forth above and immersed in an ion donation solution of 0.025N sulfuric acid wherein the sample is the 9 anion ppm standard, the recovery results are shown in Table I.

TABLE I

| | Anion | ppm | % Recovery | |
|---|---|---|---|---|
| | | | 2nd ml | 3rd ml |
| 1. | Fluoride | 1 | 110 | 120 |
| 2. | Carbonate | 5 | 13 | 15 |
| 3. | Chloride | 2 | 96 | 100 |
| 4. | Nitrite | 4 | 88 | 92 |
| 5. | Bromide | 4 | 96 | 105 |
| 6. | Nitrate | 4 | 104 | 108 |
| 7. | Phosphate | 6 | 97 | 107 |
| 8. | Sulfate | 4 | 177* | 113 |
| 9. | Iodide | 4 | 99 | 83 |

Figure 5A:
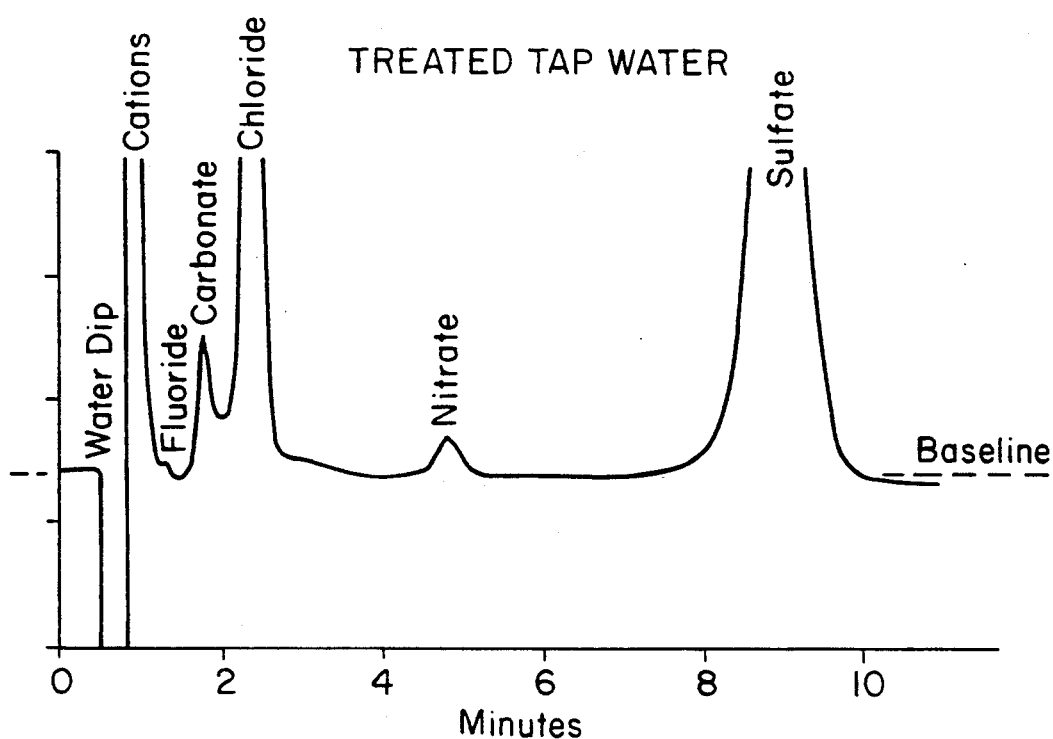
FIGS. 5a-5b are ion chromatograms of tap water passed through two sulfonated perfluorinated polymeric ion exchange hollow fibers in series immersed in 25 mM octane sulfonic acid and then 50 mM sodium octane sulfonate and that of untreated tap water.
Figure 5B:
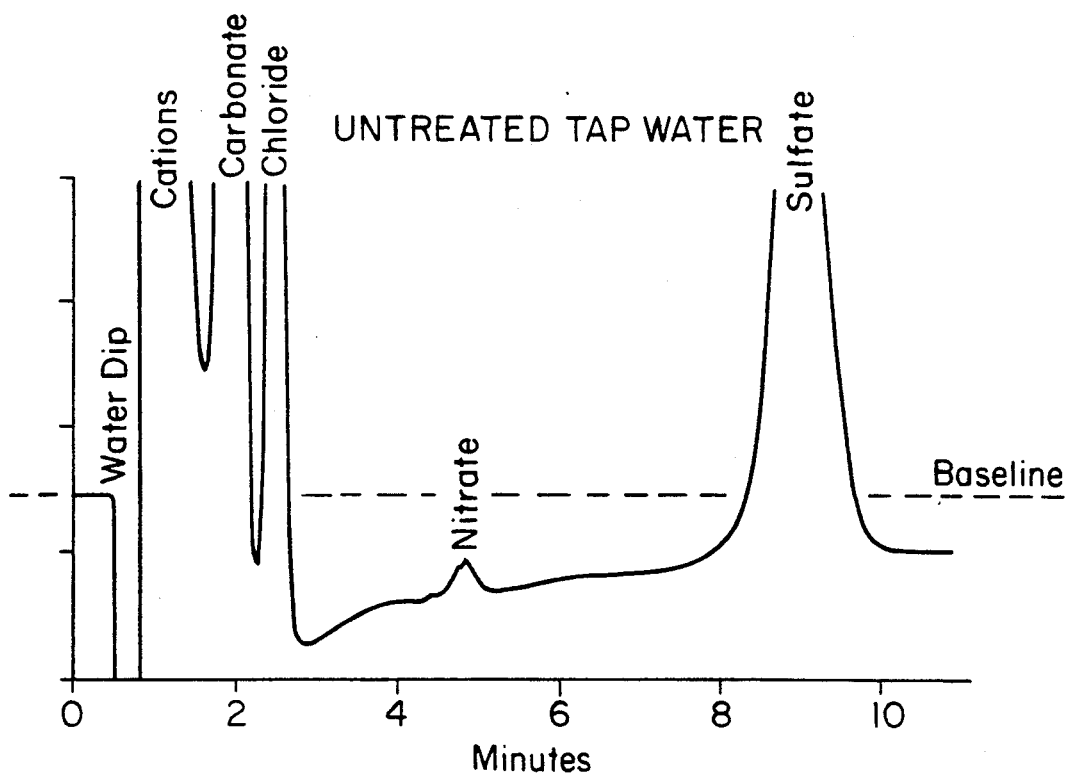

Utilizing the process of this invention, the results obtained by passing a tap water sample collected from the city of Santa Cruz, Calif. are shown. In FIG. 5b, the ion chromatographic separation obtained with untreated city water is shown. Shown in FIG. 5a, is the chromatogram of a sample treated by passing a water sample through a proton form of a Nafion fiber immersed in octane sulfonic acid followed through a sodium form of a Nafion fiber immersed in sodium octane sulfonate and having an outer diameter of 20 thousandths of an inch and an inner diameter of 14 thousandths of an inch. A very clean separation is obtained after a second step in which a sodium containing CID solution was applied.

Figure 6A:
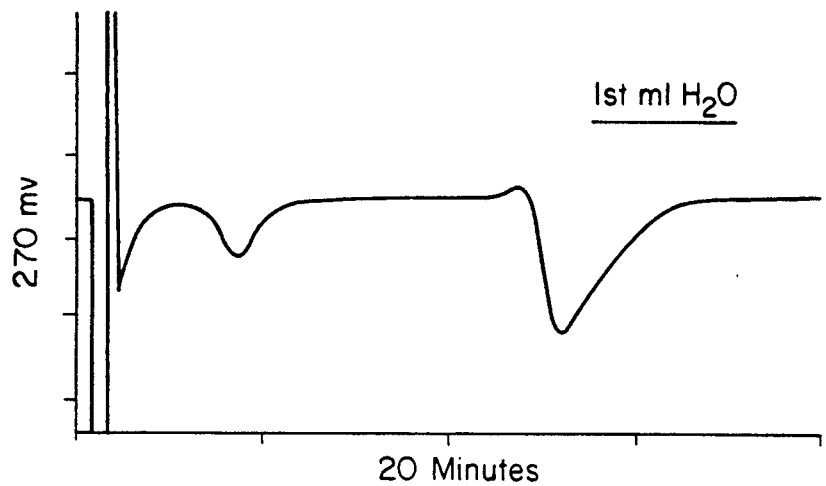
FIGS. 6a and 6b are ion chromatograms of deionized water passed through a sulfonated perfluorinated polymeric ion exchange hollow fiber immersed in 50 mM sodium octane sulfonate.
Figure 6B:
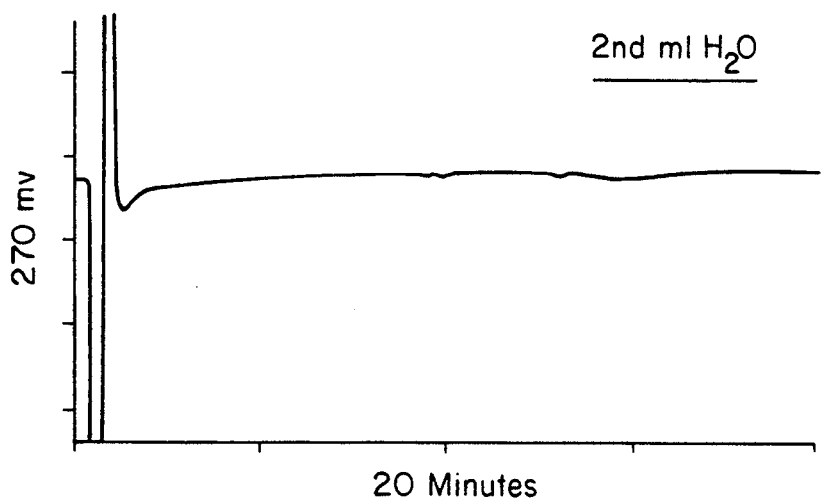

Referring to FIGS. 6a and 6b, ion chromatograms are shown to illustrate that the sodium form of a sulfonated Nafion fiber immersed in sodium octane sulfonate can be washed with only 1 ml deionized water or sample in order to remove leachable components in the fiber.

Figure 7A:
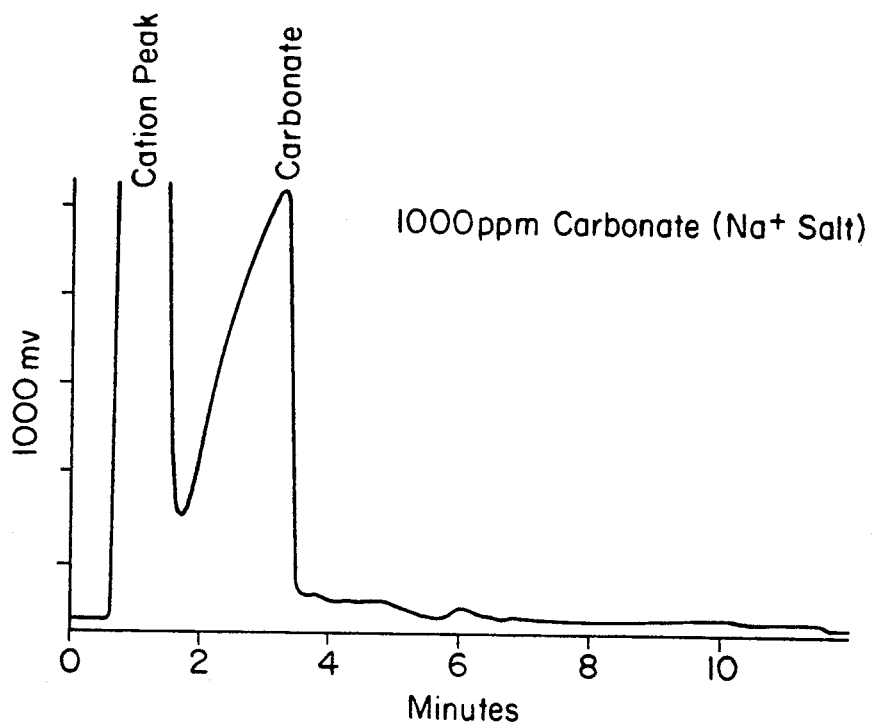
FIGS. 7a and 7b are ion chromatograms showing carbonate ion reduction in a sample in accordance with this invention.
Figure 7B:
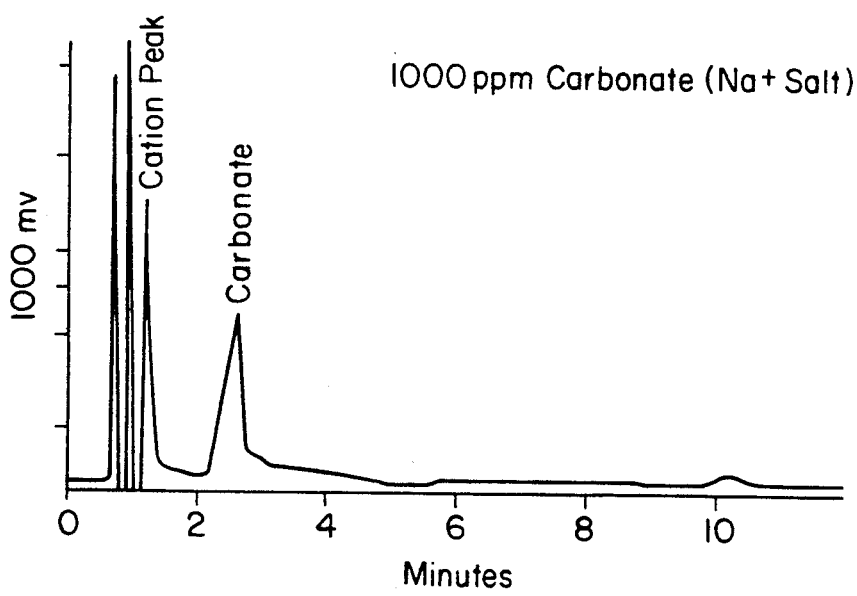

FIGS. 7a and 7b show that carbonate ion concentration in a sample containing 1000 ppm carbonate as the sodium salt is reduced by passing the sample through the sulfonated from (H+) of a Nafion hollow fiber.

Figure 8:
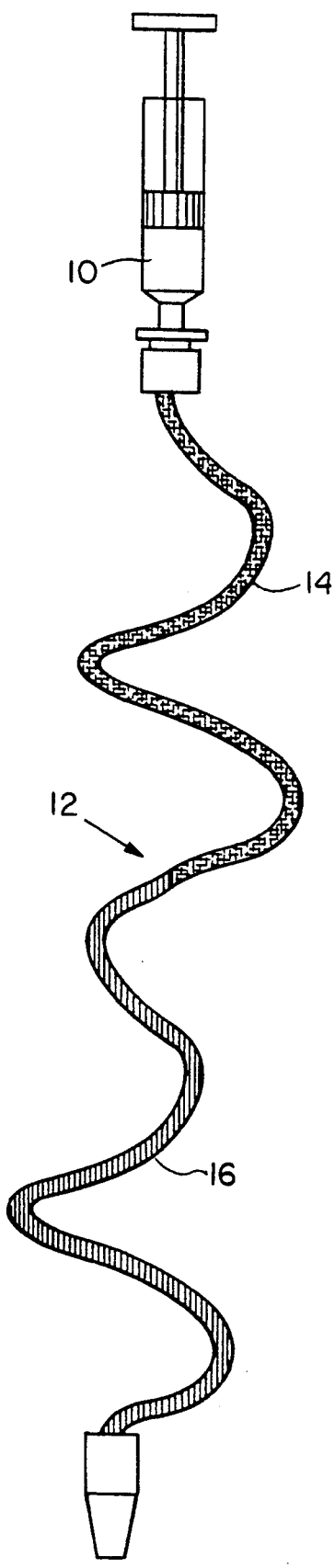
FIG. 8 shows the apparatus of this invention which utilizes a color indicator to show whether a hollow fiber is depleted of donating ion.

Referring to FIG. 8, an untreated sample is dispensed from syringe 10 into a fiber 12 coated with 4-p-anilinophenylazobenzenesulfonic acid. The fiber section 14 is yellow showing that it is depleted of hydrogen ions while the fiber section 16 is red/purple showing that it is not depleted of hydrogen ions. The fiber 12 is provided with an exit port 18 for removal of treated sample from fiber 12.

Referring to FIG. 9, the apparatus is comprised of hollow body 11, with end caps 12 and 13 respectively, hollow fiber 15 attached to connectors 14 and 16 immersed in counter ion donating solution 20. Also shown is a standard connector 14 on body component 11 and sample 25 inside syringe 17 preferably at least a portion of the hollow body is transparent so that fiber 15 can easily be viewed. Alternatively, a lid on the top of hollow body 11 adjacent to the inlet 14 can be provided to view the CIDS.

The hollow fiber 15 is attached to female connector 14 and male connector 16 such that the internal path of the fiber allows the sample 25 to proceed through the central space of the hollow fiber 15 immersed in CIDS 20 yet sample 25 is precluded from direct contact with CIDS 20 by the seamless sealed tubular structure of hollow fiber 15, and attached to connectors 14 and 16.

FIG. 10 shows a close-up of the hollow fiber 15, CIDS 20 and sample 25 in the hollow fiber undergoing a typical ion exchange process 26.

Syringe 17 with the sample to be processed 25 is attached to female luer locking port 14 by the syringe male connection member internal portion of hollow fiber 15 residing in the internal space of port 14. The CIDS is introduced into hollow body 10 and then closing the end cap.

The sample 25 is processed by hollow fiber 15 surrounded by the CIDS environment 20 within the device 10 structure as in FIG. 10. The injected sample 25 after having undergone ionic exchange 26 exits the device 10 at hollow fiber male luer lock termination 16.

CID solution 20 may also have additional components added 30 which may provide a visual indication as to the status of the CIDS 20. When the CIDS 20 becomes exhausted as after multiple injections of samples similar to sample 25, and can no longer provide additional ions to hollow fiber 15, visual indicator 30 undergoes a shift in color to indicate the absence of available donator ions in CIDS 20.

Device components, hollow body 11 with hollow fiber terminations 14 and 16, end caps 12 and 13 may be comprised of inert non ionic polymeric materials such as polypropylene to provide a rigid, clean seated, ion free supporting structure to house hollow fiber 15, CIDS 20 and indicator 30. Outlet port 16 is structured to provide a standard make luer lock geometry to facilitate attachment to numerous accessories such as extension tethers, filters, pipette adaptors, and the like to aid in device use and attachment to various configurations of chromatographic equipment.

The present invention also can utilize an arrangement of flat membranes closely positioned to each other with spaces between adjacent membranes for passage of sample therethrough. The membranes are enclosed by a housing of appropriate design with inlet and outlets being provided at opposite ends of the spaces thereby to properly direct the sample through the sample treatment apparatus. The membrane also can include a color indicator in the manner set forth above.

The process of this invention can be utilized in a batch mode wherein samples are injected in series into the hollow fiber, manually or automatically such as by using conventional robotics apparatus.

We claim:

1. The process for analyzing a sample containing ion species in a solution which comprises:

washing a membrane or hollow fiber formed from an ion exchange polymer to remove substantially all water leachable species from said polymer and to form a washed ion exchange polymer, said washed ion exchange polymer being capable of exchanging a bound cation for a cation in solution while substantially avoiding the introduction of water-leachable species in solution, passing said sample into contact with said washed ion exchange polymer, said washed ion exchange polymer being immersed in a counter ion donating solution for donating cations comprising said bound cations while avoiding contact of said sample with said counter ion donating solution, and introducing the sample contacted with said polymer into an ion analysis system.

2. The process of claim 1 wherein said membrane or hollow fiber is immersed in a counter ion donating solution containing alkali metal ions.

3. The process of claim 1 wherein two ion exchange polymers are arranged in series, one of said polymers being immersed in a counter ion donating solution including protons and the other of said polymers being immersed in a counter ion donating solution containing metal cation.

4. The process of any one of claims 1, 2 or 3 wherein said polymer has sulfonic groups.

5. The process of any one of claims 1, 2 or 3 wherein said polymer has carboxylic groups.

6. The process of claim 1 wherein said membrane or hollow fiber is immersed in a counter ion donating solution containing a water soluble sulfonated or carboxylated polymer.

7. The process of claim 1 wherein said bound cation is a transition metal.

8. The process of claim 1 wherein said bound cation is barium or any other alkaline earth cation.

9. The process of claim 1 wherein said bound cation is lead.

10. The process of claim 1 wherein said bound cation is bismuth.

11. The process of claim 1 wherein said bound cation is a metal of lanthanide or actinide series.

12. The process for analyzing a sample containing ion species in a solution which comprises:

washing a membrane or hollow fiber formed from an ion exchange polymer to remove substantially all water leachable species from said polymer and to form a washed ion exchange polymer, said washed ion exchange polymer being immersed in a counter ion donating solution for donating ions comprising said bound ions while avoiding contact of said sample with said counter ion donating solution, said washed ion exchange polymer being capable of exchanging a bound anion for an anion in solution, while substantially avoiding the introduction of water leachable species in solution, passing said sample in contact with said washed ion exchange polymer and introducing the sample contacted with said polymer into an ion analysis system.

13. The process of claim 7 wherein said membrane or hollow fiber is immersed in a counter ion donating solution containing hydroxyl ions said ion exchange polymer being capable of exchanging a bound anion for anion in solution.

14. The process of any one of claims 12 or 13 wherein said polymer is aminated.

15. The process of claim 7 wherein two ion exchange polymers are arranged in series, one of said polymers being immersed in a counter ion donating solution containing hydroxyl ion and the other of said polymers being immersed in a counter ion donating solution containing a second anion.

16. The process for preparing a sample containing ion species in a solution which comprises passing said sample into contact with a membrane or hollow fiber formed from a first ion exchange polymer capable of exchanging bound hydrogen ion for a cation in solution, while substantially avoiding the introduction of water leachable species in solution, said first ion exchange polymer being immersed in a first solution for donating hydrogen ions while avoiding contact of said sample with said first solution, passing said sample into contact with a membrane or hollow fiber formed from a second ion exchange polymer capable of exchanging bound hydroxyl for an anion in solution, while substantially avoiding the introduction of water leachable species in solution, said second ion exchange polymer being immersed in a second solution for donating hydroxyl ions while avoiding contact of said sample with said second solution, said ion exchange polymers being prewashed to remover substantially all water leachable species from said polymer, and introducing the sample contacted with said polymer into an ion analysis system.

* * * * *